United States Patent
Anand et al.

(10) Patent No.: US 9,351,708 B2
(45) Date of Patent: May 31, 2016

(54) AUTOMATED DOPPLER VELOCIMETRY USING A LOW-COST TRANSDUCER

(75) Inventors: Ajay Anand, Fishkill, NY (US); John Petruzzello, Carmel, NY (US); Rajendra Singh Sisodia, Bhopal (IN); Lalit Gupta, Noida (IN); Pallavi Vajinepalli, Bangalore (IN); Celine Firtion, Surat (IN)

(73) Assignee: Koninklijke Philips N.V., Eindhoven (NL)

( * ) Notice: Subject to any disclaimer, the term of this patent is extended or adjusted under 35 U.S.C. 154(b) by 225 days.

(21) Appl. No.: 13/995,569

(22) PCT Filed: Dec. 16, 2011

(86) PCT No.: PCT/IB2011/055729
§ 371 (c)(1),
(2), (4) Date: Jun. 19, 2013

(87) PCT Pub. No.: WO2012/085788
PCT Pub. Date: Jun. 28, 2012

(65) Prior Publication Data
US 2013/0274607 A1  Oct. 17, 2013

Related U.S. Application Data

(60) Provisional application No. 61/425,866, filed on Dec. 22, 2010.

(51) Int. Cl.
*A61B 8/00* (2006.01)
*A61B 8/08* (2006.01)
(Continued)

(52) U.S. Cl.
CPC ............. *A61B 8/5223* (2013.01); *A61B 5/489* (2013.01); *A61B 8/06* (2013.01); *A61B 8/0891* (2013.01);
(Continued)

(58) Field of Classification Search
CPC ........ A61B 8/06; A61B 8/488; A61B 8/5223; A61B 8/0891; A61B 8/4427; A61B 8/4444; A61B 5/489; A61B 8/54; A61B 8/585; A61B 8/466; A61B 8/483; A61B 8/467; G01S 15/8984; G01S 15/8988; G01S 7/52071
USPC .................................................. 600/437–469
See application file for complete search history.

(56) References Cited

U.S. PATENT DOCUMENTS 6,503,202 B1 * 1/2003 Hossack .................. A61B 8/13
600/454
8,647,259 B2 * 2/2014 Arneson .................. A61B 8/12
600/109

(Continued)

FOREIGN PATENT DOCUMENTS

| EP | 0933063 A1 | 8/1999 |
| EP | 1152364 A2 | 11/2001 |
| JP | 2007222291 A | 9/2007 |
| JP | 2008212746 A | 9/2008 |
| WO | 2011058471 A1 | 5/2011 |

OTHER PUBLICATIONS

Gogate, Sharad "Intra-Uterine Growth Restriction—Obstetrician's Perspective", International Journal of Diabetes in Developing Countries, 2001, vol. 21, Issue 1, pp. 51-56.

*Primary Examiner* — Sanjay Cattungal

(57) ABSTRACT

An automatic, stand-alone, hand-held ultrasound blood-vessel examination device includes a reduced number of transducer elements and presents a simplified user interface, without the need for displaying an image of any of the vessels. The probe, in one embodiment, acquires and examines a volume of interest, searches for a target vessel, tests the vessel for normality of blood flow, and reports the diagnosis, all automatically and without need for user intervention. In another embodiment, the probe finds a body vessel in a volume, and extracts a clinical Doppler parameter, all automatically and without need for user intervention.

11 Claims, 3 Drawing Sheets

(51) Int. Cl.
*A61B 5/00* (2006.01)
*A61B 8/06* (2006.01)

(52) U.S. Cl.
CPC ............. *A61B 8/4427* (2013.01); *A61B 8/4444* (2013.01); *A61B 8/488* (2013.01); *A61B 8/54* (2013.01); *A61B 8/585* (2013.01); *A61B 8/466* (2013.01); *A61B 8/467* (2013.01); *A61B 8/483* (2013.01)

(56) References Cited

U.S. PATENT DOCUMENTS

2014/0213905 A1* 7/2014 Saad .................... G01S 15/8984
 600/441
2014/0221838 A1* 8/2014 Loupas ............... G01S 15/8984
 600/454

* cited by examiner

AUTOMATED DOPPLER VELOCIMETRY USING A LOW-COST TRANSDUCER

FIELD OF THE INVENTION

The present invention relates to examining a volume of interest for a body vessel and, more particularly, to using ultrasound for the examining.

BACKGROUND OF THE INVENTION

Assessing the well being of fetus is a very important clinical practice in pregnancy care. Currently, the most prevalent ways for doctors to assess fetal well-being are the analysis of fetal heart rate using a cardio-tocograph (CTG) and the assessment of maternal and fetal blood vessel flows using ultrasound Doppler. Ultrasound Doppler waveform analysis of specific blood flows of fetus and mother is part of established medical practice, and a standard recommendation in various clinical guidelines for the diagnosis and assessment of high-risk pregnancies (type-2 diabetes, hypertension or pre-eclampsia in mother and IUGR—intra-uterine growth restriction of fetus). One of the main aims of routine antenatal care is to identify the "at risk" fetus in order to clinically intervene, thereby reducing the incidence of perinatal morbidity and mortality. Some of the vessels useful in the assessment of fetal well-being are: the umbilical artery, the middle cerebral artery, the ductus venosus, and the (left and right) uterine arteries and umbilical veins.

Ultrasound scanners have become indispensible in the monitoring of pregnancies worldwide. They currently provide the best option to monitor the growth and development of the fetus. Duplex ultrasound scanners provide ultrasound pulsed wave Doppler in addition to the regular scan. Color and power Doppler are newer additions to the range of scanners that provide for vascular imaging. Color Doppler, in particular, is commonly provided, resulting in what is often called a "triplex" scanner.

Doppler exams typically require a great degree of skill to obtain a clinically useful measurement. For example, correct orientation of the probe with respect to the vessel is essential to ensure that the beam-flow angle is less than 60 degrees. Errors in measurements are amplified when angles of greater than 60 degrees are used in the determination of velocities. The standard workflow on a clinical ultrasound scanner allows a sonographer to determine the orientation of the probe with respect to the vessel using a standard B-mode and Color Flow display. The spectral Doppler measurements are then obtained thus ensuring that the measured velocities are correct.

The use of ultrasound in vascular applications to perform Doppler velocimetry requires availability of skilled personnel.

SUMMARY OF THE INVENTION

In emerging market countries such as India, the shortage of specialists limits the availability and access to ultrasound. Hence, an automated method of acquiring and evaluating Doppler signals for clinical diagnosis (without requiring the user to interpret an ultrasound scan image) would be useful to non-radiologists such as OB/GYN or cardiologists who are the primary treatment providers.

In addition, a low-cost system is essential to provide an attractive solution in emerging market environments. Devices that are currently available in the market for antenatal check-ups and labor are the ultrasound and CTG machines. However, both of these devices are relatively expensive.

There exists a need for low-cost, easy-to-use solution to provide Doppler velocimetry to screen and monitor high risk pregnancies.

The present invention is directed to addressing one or more of the above-discussed concerns.

In accordance with the present invention, an ultrasound device is designed for carrying out a series of steps automatically and without need for user intervention. These steps include examining, using ultrasound, a volume for body vessels present; and, if one or more vessels are found in the examining, selecting, for fluid-flow analysis, a vessel from among the one or more vessels. This device can be engineered for low cost, as detailed further herein below.

In an aspect of the invention, the steps further include generating, for the analysis, information particular to the selected vessel.

In another aspect, the generated information includes a quantitative characteristic of a waveform. The waveform is representative of magnitude, over time, of velocity of fluid in the selected vessel.

In a further aspect, the steps include the examining, selecting, and generating, and further include performing the analysis of the generated information. A further included step is: subject to a result based on the analysis, providing, based on the generated information, an indication as to normality of fluid flow in the selected vessel.

In a still further aspect, the steps include the examining and selecting, and further include, at least until the providing is performed, repeating a sequence of steps for, with the selected vessel serving as a current vessel, each next vessel from among the vessels found. The steps of the sequence are: the selecting, the generating, performing the analysis, and the providing.

In yet another aspect, the steps include classifying the selected vessel based on the generated information, with the providing being subject to a result of the classifying.

In a supplementary aspect, prior to the examining, a target vessel within a vessel category is designated, the category being based on physiology. Based on the generated information, it is determined whether the selected vessel matches the target vessel.

In a related aspect, the examining and selecting is followed by using ultrasound to generate information particular to the selected vessel and providing, based on the generated information, an indication as to normality of fluid flow in the selected vessel.

In a different aspect the device is implemented as a handheld, stand-alone device.

In a still different aspect, the device is implemented as one or more integrated circuits.

From an alternative aspect, a device includes a two-dimensional transducer comprising elements for examining, using ultrasound, a volume for body vessels present. The elements are arranged at a spacing of at least one wavelength of ultrasound emitted from the elements in the examining.

In an associated aspect, the device is configured for automatically drawing a conclusion based upon a result of the examining.

In a sub-aspect, the drawing comprises deciding, based on the examining, as to normality of fluid flow in a vessel found in the examining.

In one other sub-aspect, the device is configured for selecting, for fluid-flow analysis, from among one or more vessels found in the examining, the drawing being based on a result of the analysis.

In a yet further sub-aspect, the device is configured for the selecting of an artery and for the selecting of a vein.

In yet another aspect, the device is configured without electronic focusing of ultrasound and without need for display of an image of any of the vessels.

In a different, alternative aspect, the elements have respective ultrasound-receiving faces each having a surface area of at least 10 square millimeters.

In an additional aspect, the faces each have a surface area of at least 25 square millimeters.

In one further additional aspect, the spacing is a spacing of at least two wavelengths of the ultrasound.

In one further alternative aspect, an ultrasound device is configured for carrying out a series of acts, the series comprising: examining a volume to find a body vessel; and, extracting, from a body vessel found in the examining, a clinical Doppler parameter, the series being performed automatically and without need for user intervention.

Details of the ultrasound examination device are set forth further below, with the aid of the following drawings.

DETAILED DESCRIPTION OF EMBODIMENTS

Figure 1:
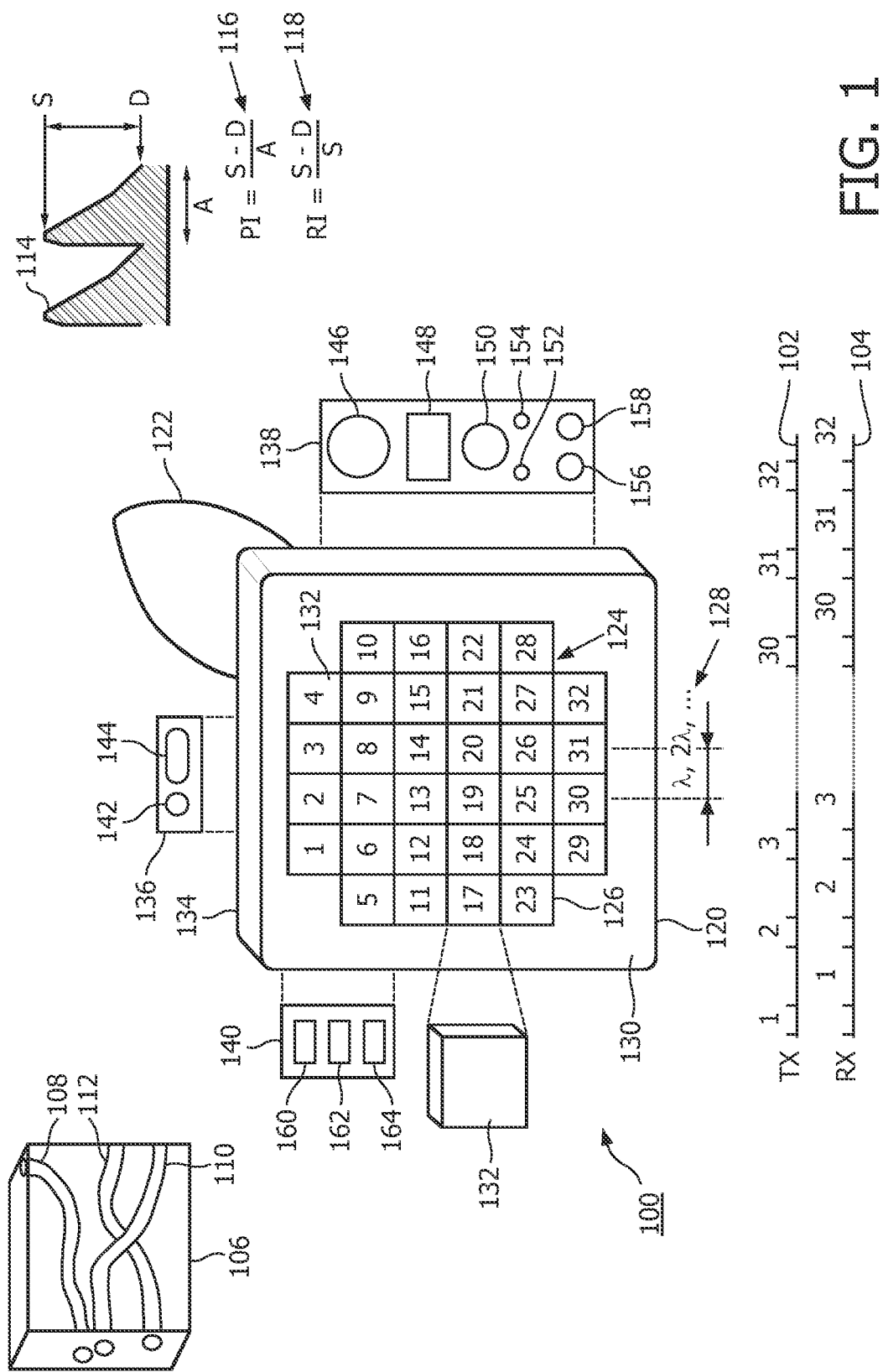
FIG. 1 is a schematic diagram showing, by example, an ultrasound probe, transmit/receive timing diagrams, a volume of interest containing blood vessels, and a blood-flow waveform and respective clinical Doppler indices in accordance with the present invention.

FIG. 1 depicts, by way of illustrative and non-limitative example, an ultrasound probe 100, transmit/receive timing diagrams 102, 104, and a volume or "volume of interest" 106 containing blood vessels 108, 110, 112. Further depicted are a blood-flow, or "spectral Doppler ultrasound", waveform 114 and respective clinical Doppler indices 116, 118.

The probe 100 is implementable as an automatic, hand-held, stand-alone, self-contained, ultrasound examination device. It has a transducer housing 120 and a handle 122.

Within the transducer housing 120, a non-phased, two-dimensional transducer 124 is comprised of transducer elements 126, the number of elements being determined by the scan volume and anatomy.

As seen in FIG. 1 by way example, the number of elements 126 is 32. Thus, with an element size of 10 mm, an approximately 6 cm×6 cm volume is covered. Flush with a front surface 130 of the housing 120, are ultrasound-receiving faces 132 of the transducer elements 126, the same faces also transmitting, i.e., issuing, ultrasound.

The total of merely 32 elements 126 stands in stark contrast to the much greater number of elements that would be required in conventional medical imaging to cover the same 6 cm×6 cm volume.

In this regard, electronic focusing for medical imaging, as with a phased-array transducer, requires an inter-element spacing of ½ wavelength, i.e., ½λ, or less. Doppler ultrasound for imaging can typically range from between $2\times10^6$ and $4\times10^6$ cycles per second (2 to 4 MHz). Ultrasound travels through soft body tissue at a speed of about 1540 meters/second. Wavelength, i.e., λ, is equal to velocity divided by frequency. Here, this is 1540 m/s divided by approximately $2\times10^6$ cycle/s=0.8 millimeter. Medical ultrasound imaging for a display would therefore require an inter-element spacing of less than 0.4 mm, and an element surface area of less than $(0.4 \text{ mm})^2$ which is less than 0.2 mm$^2$. Therefore, with a small element size on the order of ½λ, thousands of elements 126 would be required to build a 2D array that, like the one seen in FIG. 1, covers a volume of 6 cm by 6 cm.

The spacing (size) of elements in FIG. 1 is 10 mm, which, as discussed above, would ordinarily be more than 12λ of ultrasound used in examining the volume of interest 106 for the blood vessels 108, 110, 112 present.

More generally, the elements 126, in accordance with what is proposed herein, are spaced apart by more than ½λ, although inter-element spacing 128 may be λ, 2λ or more, as discussed hereinabove. The area of the face 132 is, correspondingly, at least 0.6 square millimeters (mm$^2$), and may be more, such as 10 mm$^2$, 25 mm$^2$, or 100 mm$^2$ as in FIG. 1.

Advantageously, the automatic ultrasound device 100 does not rely on display of medical images to reach a diagnosis; but, instead, features an array composed of fewer transducer elements and therefore fewer channels. Thus, cost of production is low, while, by virtue of automatic operation, reliability is maintained. Reliability may even be improved, as when medical examinations must be performed at a quicker pace. The automatic operation also tends to reduce examination time, thereby relieving workload, and making the examination more convenient.

During Doppler data acquisition, the elements 126 are fired either sequentially, as shown by the timing diagrams 102, 104, or in groups taking care that the acoustic signal from one element does not affect others that are excited at the same time. As seen in FIG. 1, the receive period lags element-by-element the transmit period for a given element, denoted by the number from 1 to 32. The Doppler receive gate is correspondingly positioned in the receive period so as to enable sampling from a corresponding depth within the volume of interest 106.

On a back surface 134 of the housing 120, so as to face the user, are a number of user-interface, input-output panels which include a top panel 136, a left panel 138 and a right panel 140. An on-off switch 142 and an audio speaker face 144 are disposed in the top panel 136. The left panel 138 frames a function navigation/actuation button 146, a display 148, a Doppler power detection indicator 150, fetal heartbeat acquisition indicator 152, a maternal heartbeat acquisition indicator 154, a normal blood-flow indicator 156, and an abnormal blood-flow indicator 158. The right panel 140 includes three initializing-parameter-entry feedback windows 160, 162, 164.

Clinical Doppler indices, such as the pulsatility index (PI) 116 and the resistance index (RI) 118 are Doppler angle-independent measures of blood pulsatility. The symbols S, D and A represents, respectively, the peak systolic frequency shift, the end diastolic frequency shift, and one cardiac cycle. This is seen from the blood-flow waveform 114 which is a graph of Doppler frequency, and thus blood flow velocity, versus time.

The probe 100 can utilize both indices PI and RI in identifying blood vessels and in assessing normality of blood flow. Within the probe 100, control circuitry (not shown), serving as the present ultrasound device, can take the form of one or more integrated circuits (ICs). One or more ICs, alternatively, be configured for installation into existing apparatus such as ultrasound Duplex scanners.

Figure 2:
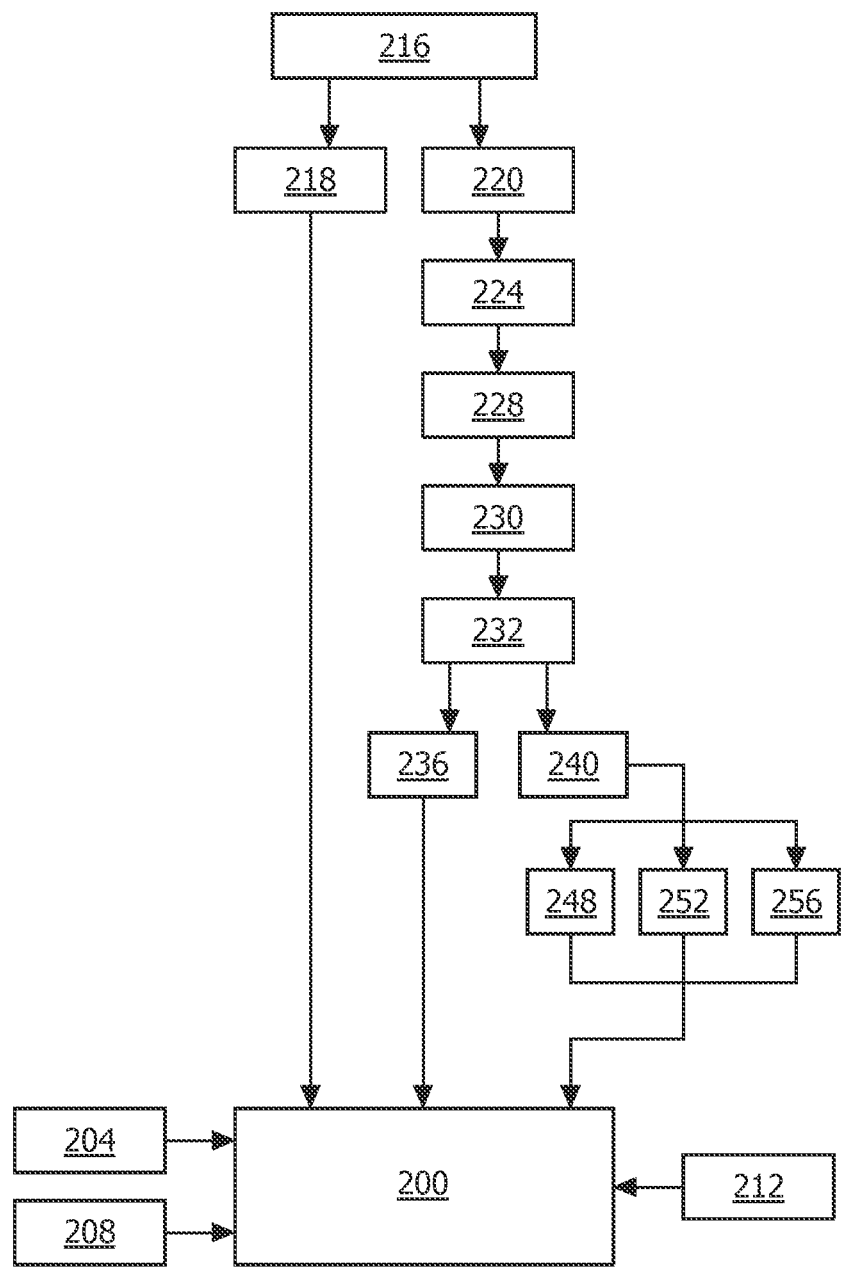
FIG. 2 is a conceptual flow diagram of exemplary signal processing in accordance with the present invention.

The signal processing involved in classifying a blood vessel 108-112 found by the probe 100 in the volume of interest 106 is shown, by example, in FIG. 2.

A blood vessel classifier 200 can be implemented as a k-nearest neighbor (K-NN) classifier, with K=3 for example.

The classifier is first used to predict whether the vessel 108-112 is a vein or artery. Various feature inputs to the classifier 200, such as the PI, are used, each of the M types of input corresponding to a dimension in M-dimensional feature space. Another type of input to the classifier is training examples. Each training example corresponds to an actual clinical case, and includes the M feature inputs for that case, defining the example as a particular point, i.e., "example point", in the M-dimensional space. With each example point is associated the respective outcome of "vein" or "artery", depending upon whether that training example actually pertained to a vein or to an artery. The classifier 200 having been initialized with the training examples, a point in M-dimensional space is formed using the feature inputs derived for the blood vessel 108-112 currently being classified. For K=3, the 3 closest neighbor (example) points are identified. Each neighbor will have as its outcome either the value "artery" or "vein." The majority vote prevails. There are never any ties since 3 is an odd number.

If the vessel is classified as an artery, the classifier 200 next determines whether it is maternal or fetal, by the same nearest neighbor algorithm. If the blood vessel is a maternal artery, a determination is made as to whether it is a uterine artery. If, on the other hand, the vessel is a fetal artery, a determination is made as to whether it is the umbilical artery. The latter two determinations use the same nearest neighbor algorithm.

Nearest neighbor classifiers enjoy the benefit of simplicity, although other alternative methods such as neural networks, or support vector machines (SVMs), could be used instead.

Classifier inputs from the user include the gestational age 204, and a rough, approximate location 208 of the probe on the mother's abdomen. A vascular model 212 in the form of training examples for the classifier 200 is also provided.

Other inputs come directly or indirectly from the pulse-echo information from received ultrasound 216.

Directly from the ultrasound 216, an average reflective index estimation 218 is made for the tissue around the probe 100. This index is compared to a pre-defined reflection index list to determine the position of the probe 100 on the mother's body.

To form indirect inputs, the ultrasound received is demodulated in a demodulator 220 to extract an ultrasound Doppler signal 224 from the carrier frequency. A fast Fourier transform (FFT) 228 is performed on the Doppler signal 224 to generate a spectrogram, or "FFT-based sonogram", 230. From the spectrograms 230, one or more relevant spectral profiles 232 are extracted. The term "spectral profile" signifies the part of the sonogram 230 that corresponds to blood flow through an artery or vein. The spectral profile 232 can be approximated as the region between curves corresponding to the maximum and minimum spectral velocities (or spectral frequencies). The spectral breadth 236 of the extracted spectral profile 232 is estimated and provided to the classifier 200. From the spectral profile(s) 232, a curve 240 corresponding to the peak (or, alternatively, the average) spectral velocities is extracted. Specific temporal features 248 are also extracted from the spectral profile(s) 232. These features include, for example, the presence of a notch immediately preceding the pulse in the blood flow waveform 114 of a uterine artery. The PI and RI for the vessel about to be subject to classification 252 are also extracted. In an initialization procedure which precedes examination of the current volume of interest 106, the pulse cycle time estimation 256 is performed based on the spectral profile(s) 232 then extracted.

Figure 3A:
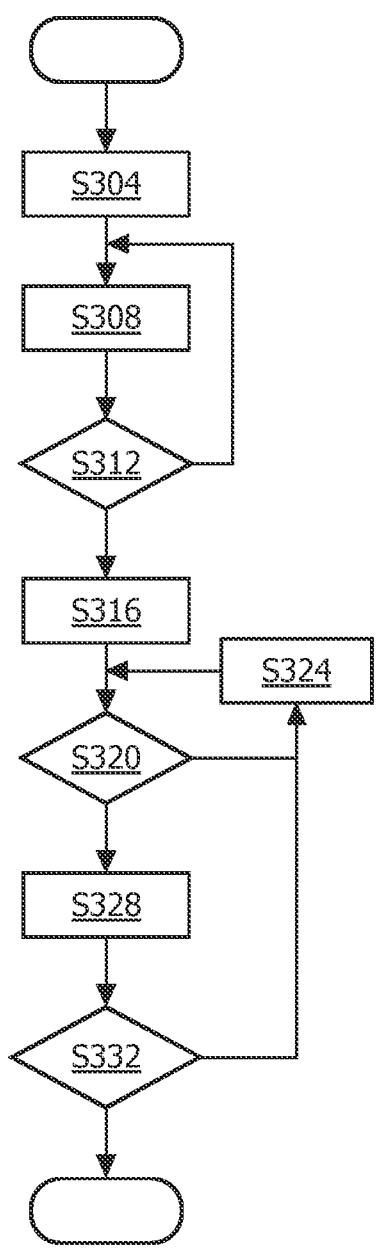
FIGS. 3A and 3B are flow charts demonstrating an example of probe operation in accordance with the present invention.
Figure 3B:
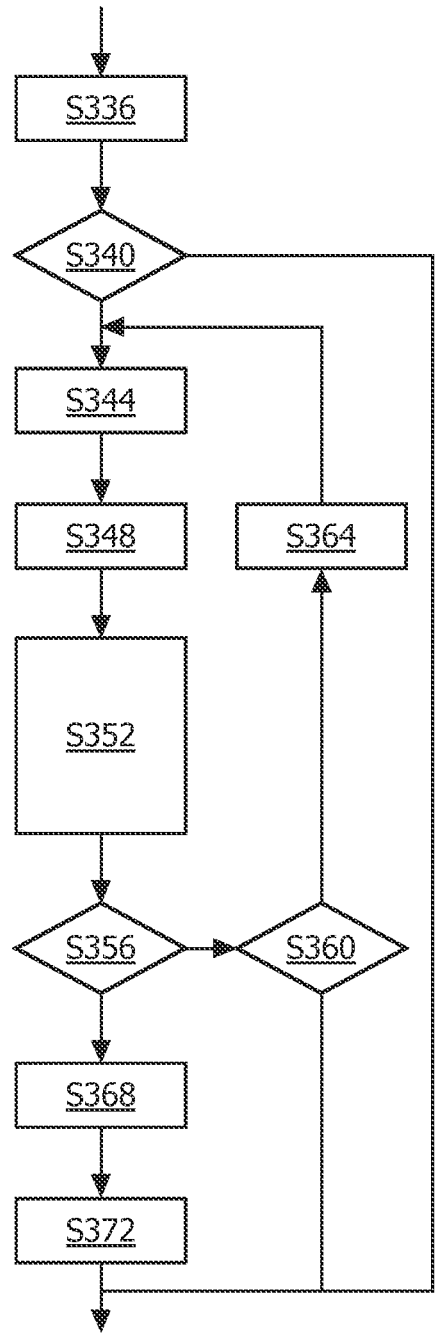

Operationally, and as shown in FIGS. 3A and 3B, the user, who may be a clinician, midwife, general practitioner, obstetrician/gynecologist or fetal radiologist, inputs, as part of the initialization procedure, a target blood vessel for examination, e.g., left uterine artery (falling within the "uterine artery" blood-vessel physiological category); gestational age; and a rough description of the location the probe will have once initialization ends and the examination begins. Specifically, after actuating the on/off switch 142, the user presses the function navigation/actuation button 146 twice in succession quickly. In response, the first blood vessel choice appears in the display 148. If the choice appearing is not the target blood vessel for examination, the button 146 is pressed once to bring up a new choice in the display 148. This is done repeatedly until the choice displayed is the one for selection. The button 148 is then held down, and the choice is echoed in the initializing-parameter-entry feedback windows 160. Appearing in the display 148 is a choice for gestational age, in months or weeks. In a similar fashion, the user navigates to the correct age, and holds down the button 146, to echo the selection to the window 162. To complete initializing-parameter entry, the same procedure is carried out for the probe location, the selected location being shown in the window 164 (step S304).

The user now continues with initialization by placing the probe on the mother's abdomen for pulse cycle time estimation 256. The user presses the function navigation/actuation button 146 to launch ultrasound Doppler operation. The transducer will scan depths at each element location to detect blood movement, i.e., Doppler power. If the Doppler power detection indicator 150 lights up, Doppler power in the frequency band of 300-1000 Hz representative of blood flow is detected that is of sufficient magnitude for concluding that a fetal or maternal heart beat can be measured from arterial blood flow. The heart beat rate of the mother is usually lower than the fetal heart beat rate. In addition to the indicator 150, a short beep may be emitted from the audio speaker 144, to alert the user to the onset of detection of Doppler power. Alternatively or in addition, audio feedback of the Doppler signal may come over the audio speaker 144. The probe 100 is held in place for several seconds; if not, the Doppler power drops and a lit indicator light 150 must again be achieved. If, at the end of the several-second period, neither the fetal nor maternal heart beat is detected, the user can move the probe to another location on the mother's abdomen, and can do this repetitively until detection occurs. If the fetal or maternal heart beat is detected, i.e., a body vessel, and in particular an artery, is found, by the signal processing route 220-232, 240, 256, the corresponding fetal heart beat acquisition indicator 152 or maternal heart beat acquisition indicator 154 is lit (step S308). The user, repetitively, moves the probe 100 to a next location on the mother's abdomen until both indicators 152, 154 are lit (step S312), indicating that the pulse cycle time, a clinical Doppler parameter, has been acquired, and extracted, for both the mother and fetus.

The user now places the probe to check for normality/abnormality of blood flow in a corresponding maternal or fetal vessel which is the target vessel (step S316). If the Doppler power detection indicator 150 does not light up (step S320), Doppler power in the frequency band of 300-1000 Hz representative of blood flow is not detected or is of insufficient magnitude for finding one or more blood vessels. In that case, the user moves or tilts the probe 100 (step S324), until the indicator 150 is lit.

Once the indicator is lit, the probe 100 is held in place for several seconds to process the volume of interest 106 (step S328).

Advantageously, this processing occurs automatically and without need for user intervention. Since the display of an image of a blood vessel is not required, no electronic focusing of ultrasound is required. The device is thereby simplified and cost-effective.

The outcome of the processing may be a green light of the normal blood-flow indicator 156, a red light of the abnormal blood-flow indicator 158, or lack of either light if the blood vessel currently being examined does not match the target vessel. If neither indicator 156, 158 is lit (step S332), processing returns to step S324.

An example of the processing in step S328 is provided in FIG. 3B. A volume of interest 106, which would change each time the probe 100 is moved or tilted, but which is fixed while the user holds the probe steady, is subject to examination for blood vessels present. In particular, the Doppler power is a frequency band of 300-1000 Hz is computed. This generates a 3-dimensional (3D) representation of vessels 108-112 in the scan volume. The total number of vessels in the scan volume is identified using continuity criteria. For example, for the 8 immediately adjacent pixels, i.e., the 4 side and 4 diagonal pixels, it is assumed that adjacent pixels for which blood flow is detected represent the same blood vessel. Yet, the blood vessels can be mapped in 3D, since the transducer receive-gates can be set for different depths. In 3D, a least-squares based line-fitting algorithm is used to find the straight line joining the points identified using the continuity criterion. The angle of the straight line from the ultrasound-receiving faces 132 of the transducer elements 126 is then computed. This results in a 3D map from which individual vessels, and their individual orientations, are identifiable. With the orientations identified, spatial features can be determined from the map. For example, in a uterine artery scan the Doppler sample volume is typically placed at the pseudo-intersection of the uterine and iliac arteries. The intersection is determined as the location of the minimum sum of the squared distances between pixels on the vessels (step S336).

If the vessel map contains no vessels 108-112 (step S340), processing of the current volume of interest 106 is complete, no diagnosis is rendered, and control proceeds to step S332.

Otherwise, if a vessel 108-112 is detected, a vessel from among those found in the volume of interest 106 is selected for fluid-flow analysis and as a candidate for matching the target vessel (step S344). Any criterion can be used for the selection, since selection of candidates does not end until the target vessel is found or all of the vessels 108-112 in the volume of interest 106 have been processed.

Information particular to the selected vessel is generated, as seen in FIG. 2 (step S348). The information includes spectral Doppler waveform characteristics (mean frequency estimate, cycle time—time interval between 2 successive peaks, spectral width—width between maximum and minimum frequency envelope at peaks and valleys), time to peak, holder's defect and clinical Doppler indices (such as, S/D, PI and RI), for example.

Based on the generated information and analysis thereof, the blood vessel classifier 200 classifies the selected vessel (step S352).

If the classification does not match the target vessel (step S356), and no next vessel from among those found in the volume of interest 106 exists (step S360), control proceeds to step S332.

Otherwise, if the classification does not match the target vessel, but a next vessel does exist, control branches back to step S344, with that next vessel serving as the selected vessel (step S364).

If, on the other hand, the classification matches the target vessel, the probe 100 draws a conclusion as to normality of the blood flow in the target, i.e., selected, vessel. In particular and by way of example, the Doppler parameters are compared with nomograms, i.e., tables representing the range of expected Doppler indices as a function of gestational age, to determine whether the flow profile is normal or abnormal (step S368).

Based on the conclusion, an indication as to normality of the blood flow in the selected vessel is provided by the green light of the normal blood-flow indicator 156 or the red light of the abnormal blood-flow indicator 158 (step S372).

Although methodology of the present invention can advantageously be applied in providing medical diagnosis for a human or animal subject, the scope of the present invention is not so limited. More broadly, techniques of the present invention are directed to finding, and subjecting to fluid-flow analysis, vessels in body tissue, in vivo, in vitro or ex vivo.

What is proposed herein pertains to an automated Doppler device for rendering a clinical diagnosis based on a result of analyzing the characteristics of spectral Doppler waveforms. Applications include carotid and renal arteries screening, ABI measurements for detecting peripheral arterial disease (PAD), transcranial, bleed detection in trauma or other hemorrhages in addition to fetal well-being assessment.

An automatic, stand-alone, hand-held ultrasound blood-vessel examination device requires a reduced number of transducer elements and presents a simplified user interface, without the need for displaying an image of any of the vessels. The probe, in one embodiment, acquires and examines a volume of interest, searches for a target vessel, tests the vessel for normality of blood flow, and reports the diagnosis, all automatically and without need for user intervention. In another embodiment, the probe finds a body vessel in a volume, and extracts a clinical Doppler parameter, all automatically and without need for user intervention.

While the invention has been illustrated and described in detail in the drawings and foregoing description, such illustration and description are to be considered illustrative or exemplary and not restrictive; the invention is not limited to the disclosed embodiments.

For example, more than one target blood vessel can be designated during initialization. These can be processed in the order they are found, or a particular order can be specified during initialization.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, and thus can be realized as register memory, processor cache or RAM, for example.

A single processor or other unit may fulfill the functions of several items recited in the claims. The mere fact that certain measures are recited in mutually different dependent claims does not indicate that a combination of these measures cannot be used to advantage.

What is claimed is:

1. An ultrasound device having a processor configured to carry out a series of acts, said series comprising acts of:
   a) examining, using an ultrasound probe of the ultrasound device, a volume to find body vessels present within the volume; and
   b) if one or more vessels are found within the volume in said examining act, then b1) selecting, for fluid-flow analysis, a vessel from among said vessels found within the volume, b2) generating, for said fluid-flow analysis, information particular to the selected vessel, b3) determining, based on the generated information, whether said selected vessel matches a target vessel, and b4) if the selected vessel matches the target vessel, then b4) (i) providing, based on the generated information, an indication as to normality of fluid flow in the selected vessel, else b4) (ii) repeating the selecting, generating, and determining with a next vessel of the vessels found, until there is no further next vessel of the vessels found within the volume,
   wherein said acts of examining and selecting (i) do not rely on a display of ultrasound scan images, and (ii) are performed automatically and without need for user intervention to interpret an ultrasound scan, and
   wherein the processor is further configured to determine, based on the generated information, whether the selected vessel is a maternal vessel or a fetal vessel.

2. The ultrasound device of claim 1, wherein the generated information comprises a quantitative characteristic of a waveform, wherein said waveform is representative of magnitude, over time, of velocity of fluid in said selected vessel.

3. The ultrasound device of claim 1, wherein the processor is further configured to perform acts of performing said fluid-flow analysis of the generated information, and, subject to a result based on said fluid-flow analysis, providing, based on said generated information, the indication as to normality of fluid flow in said selected vessel.

4. The ultrasound device of claim 3, wherein the processor is further configured to perform an act of, at least until said providing is performed, repeating, with said selected vessel serving as a current vessel, act b) for each next vessel from among said vessels found.

5. The ultrasound device of claim 3, wherein the processor is further configured to perform an act of classifying said selected vessel based on said generated information, said providing act being subject to a result of said classifying.

6. The ultrasound device of claim 1, wherein the processor is further configured to perform an act of designating, prior to said examining act, the target vessel within a vessel category, said category being based on physiology.

7. The ultrasound device of claim 1, wherein the ultrasound emitted from the elements and reflected back to the ultrasound probe is used to acquire volumetric data to be examined.

8. The ultrasound device of claim 1, wherein the ultrasound device is implemented as a hand-held, stand-alone device.

9. The ultrasound device of claim 1, wherein the ultrasound device includes one or more integrated circuits.

10. A non-transitory computer readable medium for an ultrasound body-fluid-flow analysis device, said medium comprising instructions executable by a processor of the ultrasound body-fluid flow analysis device for carrying out a series of acts, said series comprising acts of:
   a) causing an ultrasound probe to examine of the ultrasound body-fluid flow analysis device, a volume to find body vessels present within the volume;
   b) if one or more vessels are found within the volume in said examining, then b1) selecting, for fluid-flow analysis, a vessel from among said vessels found within the volume, b2) generating, for said fluid-flow analysis, information particular to the selected vessel, b3) determining, based on the generated information, whether said selected vessel matches a target vessel, and b4) if the selected vessel matches the target vessel, then b4) (i) providing, based on the generated information, an indication as to normality of fluid flow in the selected vessel, else b4) (ii) repeating the selecting, generating, and determining with a next vessel of the vessels found, until there is no further next vessel of the vessels found within the volume; and
   determining, based on the generated information, whether the selected vessel is a maternal vessel or a fetal vessel,
   wherein said acts of examining and selecting (i) do not rely on a display of ultrasound scan images, and (ii) are performed automatically and without need for user intervention to interpret an ultrasound scan image.

11. A method for ultrasound body-fluid-flow analysis, said method comprising acts of:
   configuring an ultrasound device for performing, automatically and without need for user intervention to interpret an ultrasound scan image, a series of acts, said series comprising acts of:
   a) examining, using an ultrasound probe of the ultrasound device, a volume to find body vessels present within the volume; and,
   b) if one or more vessels are found within the volume in said examining, then b1) selecting, for fluid-flow analysis, a vessel from among said vessels found within the volume, b2) generating, for said fluid-flow analysis, information particular to the selected vessel, b3) determining, based on the generated information, whether said selected vessel matches a target vessel, and b4) if the selected vessel matches the target vessel, then b4) (i) providing, based on the generated information, an indication as to normality of fluid flow in the selected vessel, else b4) (ii) repeating the selecting, generating, and determining with a next vessel of the vessels found, until there is no further next vessel of the vessels found within the volume; and
   determining, based on the generated information, whether the selected vessel is a maternal vessel or a fetal vessel,
   wherein said examining and selecting acts do not rely on a display of ultrasound scan images.

* * * * *